US010946382B2

(12) United States Patent
Davies et al.

(10) Patent No.: US 10,946,382 B2
(45) Date of Patent: Mar. 16, 2021

(54) SYSTEM, METHOD AND APPARATUS FOR CANCER DETECTION

(71) Applicant: StrandSmart, Inc., San Francisco, CA (US)

(72) Inventors: Adrianna Davies, San Francisco, CA (US); Shesh N. Rai, Louisville, KY (US); Balaji Panchapakesan, South Grafton, MA (US)

( * ) Notice: Subject to any disclaimer, the term of this patent is extended or adjusted under 35 U.S.C. 154(b) by 0 days.

(21) Appl. No.: 16/214,308

(22) Filed: Dec. 10, 2018

(65) Prior Publication Data
US 2019/0176145 A1 Jun. 13, 2019

Related U.S. Application Data

(60) Provisional application No. 62/597,270, filed on Dec. 11, 2017.

(51) Int. Cl.
G01N 33/574 (2006.01)
B01L 3/00 (2006.01)
G16H 40/63 (2018.01)
G01N 35/00 (2006.01)

(52) U.S. Cl.
CPC ............ B01L 3/508 (2013.01); G01N 33/574 (2013.01); G16H 40/63 (2018.01); B01L 2200/04 (2013.01); B01L 2300/023 (2013.01); B01L 2300/027 (2013.01); B01L 2300/0645 (2013.01); G01N 35/00871 (2013.01); G01N 2035/00891 (2013.01)

(58) Field of Classification Search
None
See application file for complete search history.

(56) References Cited

U.S. PATENT DOCUMENTS

| 2011/0224091 A1 | 9/2011 | Panchapakesan |
| 2016/0144358 A1 | 5/2016 | Patel |
| 2016/0274104 A1* | 9/2016 | Aminoff ............ G01N 21/8483 |

OTHER PUBLICATIONS

International Search Report, dated Feb. 25, 2019, corresponding PCT/US2018/64653.
Written Opinion, dated Feb. 25, 2019, corresponding PCT/US2018/64653.

* cited by examiner

Primary Examiner — Rebecca M Giere
(74) Attorney, Agent, or Firm — Van Dyke Intellectual Property Law; Raymond Van Dyke

(57) ABSTRACT

Systems, methods, techniques, devices and apparatuses for detecting cancer. A handheld device which performs an automated analysis from a droplet of whole blood for other bodily fluid. The device is inexpensive, non-invasive, easy to use, and easily transportable, enabling better screening for a wider range of diseases, enabling the detection of metastases at an earlier stage, when interventions are more effective, enabling regular monitoring of patients receiving therapy or those in remission, and enabling a major contribution to the growing body of scientific evidence on how to treat certain cancers based on information gathered about the genomic profile of a tumor. In short, the present invention saves more lives, with fewer resources, and causing minimal harm than prior art techniques.

25 Claims, 1 Drawing Sheet

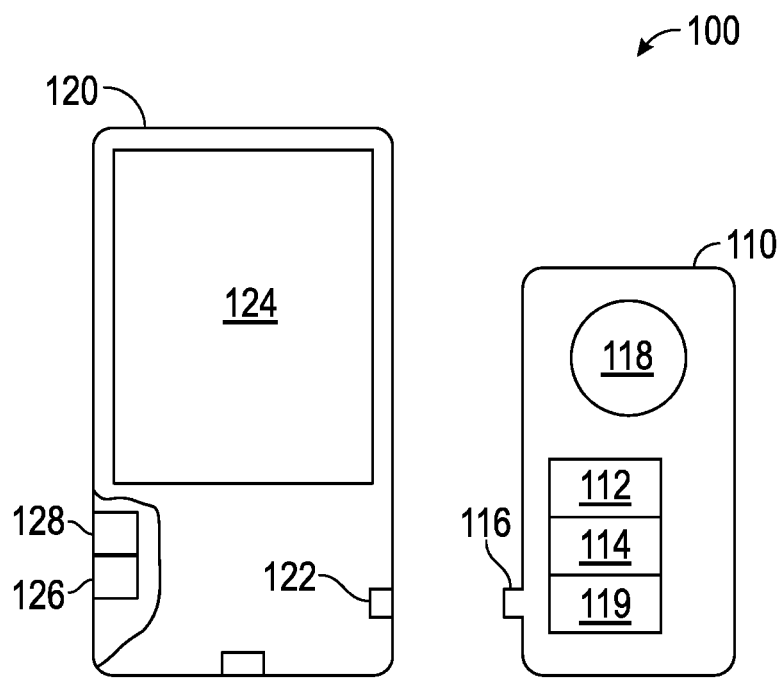
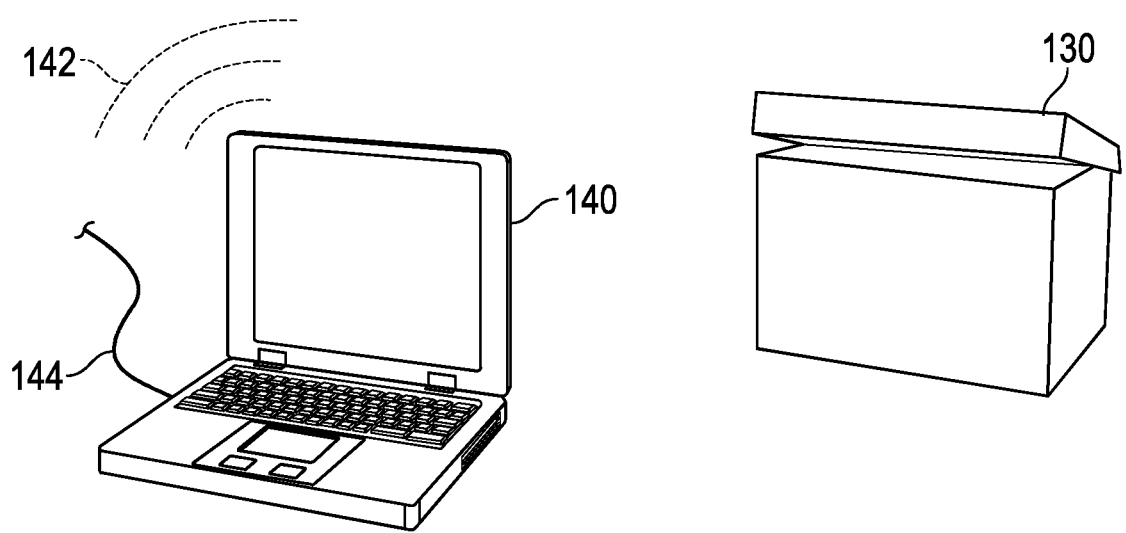

SYSTEM, METHOD AND APPARATUS FOR CANCER DETECTION

CROSS REFERENCE TO RELATED APPLICATION

The present invention is a non-provisional of U.S. Patent Application Ser. No. 62/597,270, entitled "SYSTEM, METHOD, TECHNIQUE, DEVICE AND APPARATUS FOR CANCER DETECTION ENABLED BY SMART PHONES AND TABLETS," filed Dec. 11, 2017, the subject matter of which is incorporated by reference herein.

FIELD OF THE INVENTION

The present invention is directed to improvements in the detection of cancer.

BACKGROUND OF INVENTION

There are currently more than 100 types of cancer, which are characterized by abnormal cell growth. Cancers develop from many different causes, ranging from radiation exposure, to chemicals and viruses. An individual has varying degrees of control over exposure to cancer-causing agents. As per guidelines from the American Cancer Society (ACS), only 5 total cancers are screened for currently in the United States, and these are done so according to age and risk profiles, e.g., colon, breast, cervical, prostate, and lung cancers.

Cancer is among the leading causes of death worldwide. In 2012, there were 14 million new cases and 8.2 million cancer-related deaths worldwide. The number of new cancer cases are projected to rise to 22 million within the next two decades. More than 60% of the world's new cancer cases occur in Africa, Asia, and Central and South America; 70% of the world's cancer deaths also occur in these regions. There is thus a huge unmet global need for cost effective, efficient, and accessible cancer diagnostics across the entire world.

There is, therefore, a present need to provide a system, method, technique, device and apparatus for detecting cancer and obtaining cancer information simply from a drop of blood or other bodily fluid.

SUMMARY OF THE PRESENT INVENTION

The present invention is directed to a handheld device, which performs an automated analysis from a droplet of whole blood or other bodily fluid. The device is inexpensive, non-invasive, easy to use, and easily transportable. The invention serves several purposes and goals, for example, enabling the screening of more people, and for a wider range of diseases; enabling the detection of metastases at an earlier stage, when interventions are more effective; enabling regular monitoring of patients receiving therapy or those in remission; and enabling major contributions to the growing body of scientific evidence on how to treat certain cancers based on information gathered about the genomic profile of tumors. In short, the present invention can save more lives, with fewer resources, and causing minimal harm.

BRIEF DESCRIPTION OF THE DRAWING

While the specification concludes with claims particularly pointing out and distinctly claiming the subject matter that is regarded as forming the present invention, it is believed that the invention will be better understood from the following description taken in conjunction with the accompanying DRAWINGS, where like reference numerals designate like structural and other elements, in which:

The FIGURE set forth and described in the text hereinbelow provides a representative view of various aspects and features of a portable cancer detector, system, technique, device, apparatus and methodology, employing the principles of the present invention in exemplary configurations.

FIG. 1 of the DRAWINGS generally illustrates a configuration of exemplary components for practicing the principles of the present invention.

DETAILED DESCRIPTION OF THE PRESENT INVENTION

The present invention will now be described more fully hereinafter with reference to the accompanying DRAWING set forth herein, in which preferred embodiments of the invention are shown. It is, of course, understood that this invention may, however, be embodied in many different forms and should not be construed as limited to the embodiments set forth herein; rather, these embodiments are provided so that the disclosure will be thorough and complete, and will fully convey the scope of the invention to those skilled in the art. It is, therefore, to be understood that other embodiments can be utilized and structural changes can be made without departing from the scope of the present invention.

The principles of the present invention are directed to the development of an easy to use device, system, and method for the early detection of cancer, generally designated by the reference numeral 100.

The present disclosure provides for a hand-held device for cancer detection, generally designated by the reference numeral 110, which is plugged into a smartphone, generally designated by the reference numeral 120, to operationalize the invention. The present invention is preferably delivered as a sealed kit, which is generally designated by the reference numeral 105, which includes one or more of the aforesaid devices 110 therein.

Each kit 105 preferably contains: 1) Instructions for use; 2) A finger pricking device; 3) Antiseptic wipes; 4) A cartridge plug-in device 110 embedded with antibodies for a specific, or multiple cancer biomarkers, generally designated by the reference numeral 112; and 5) a storage vehicle, generally designated by the reference numeral 130, with at least one stabilizing agent to maintain sample integrity for further analysis via transport.

When a kit 105 is ordered the physician or consumer may specify the phone jack (iPhone, Android or other smartphone 120) configured to receive the cartridge 110. It should be understand that instructions for the accompanying mobile software application, or app, as well as for the testing, may be downloaded from Apple, Google play or from another source via the Internet.

The present disclosure preferably provides for a handheld device, apparatus, system, technique and methodology, generally illustrated with regard the reference numeral 100, to enable a cancer biopsy or other testing utilizing a smartphone 120. In a preferred embodiment of the present invention, a nanotube wafer chip, generally designated by the reference numeral 114, is embedded on a rectangular cartridge 110, with an adapter, generally designated by the reference numeral 116, designed for any smart phone jack or port, generally designated by the reference numeral 122.

A droplet of whole blood (or other amounts from other selected bodily fluid) from a patient is placed on an indicated area for blood or fluid deposition, generally designated by the reference numeral 118, of the cartridge 110 to detect the presence of circulating tumor cells (CTCs) or other cancer indicators. If a cancer cell (or a cell indicative of cancer) is detected, a signal will render on the mobile software application, e.g., as shown on a screen, generally designated by the reference numeral 124, accompanying the device in a short period of time, e.g., 10 minutes. The time will be reduced to 5 minutes as further iterations of the device are developed. The rise in electrical signal is a result of multiple-antibody-cell receptor interaction, which is picked up, analyzed and measured, and the displayed.

A core embodiment of the device is the aforementioned plug-in cartridge 110 embedded with a nanotube chip 114, which performs an automated analysis, e.g., an automated liquid biopsy, based on electrochemical detection of the presence of a circulating tumor cell (or other indicia for cancer). The cartridge 110 is embedded with a nanotube chip 114, and a droplet of whole blood (or other bodily fluid) is placed directly on the indicated area 118 of the cartridge 110 after following the finger pricking or other protocol for fluid collection. In most cases the test will be administered by a medical professional, such as a hospital nurse.

Test kits 105, e.g., the cartridges 110 and other items for use with a smart phone 120 (or other computing device) can be ordered by a consumer for home use only with a physician's order. Given the potential for human error with self-sampling and the gravity of a false result, test kits 105 for home use by a consumer are clearly labelled and have instructions that these kits are not intended to provide a diagnosis. If the consumer test detects a cancer cell they must immediately contact their physician and schedule a visit to obtain a formal cancer diagnosis. Kits 105 are intended to have the ease of use as current diabetes blood testing kits The chip 114 itself preferably has fine connections running from each microelectrode therein to a central analog-to-digital board, generally designated by the reference numeral 119, or converter. The accompanying mobile application software is coded to analyze the bits and display the result on the phone or other device 120, connected thereto either through wireline or wireless.

The kit 105 cartridges 110 are designed preferably for single use. Cartridges 110 can be purchased for specific cancer types. Depending on the cancer type of interest, the cartridge 110 is pre-embedded with relevant antibodies for biomarkers 112 of the specified cancer indication of interest. For example, a breast cancer cartridge would be embedded with antibodies targeting cancer cells with expression of human epidermal growth factor receptor-2 (HER2/neu, c-erbB2) (HER-2), epithelial cell adhesion molecule (Ep-CAM), epidermal growth factor receptor (EGFR), and Vimentin, either alone or in combination, and other factors.

The cartridge 110 is also designed for primary cancer detection and metastatic cancer. Patients who have undergone chemotherapy and hormonal therapy can monitor and check the cancer remission through this testing. The present invention is adaptable to the employment of any number of testing protocols so long as the cancer test can be reduced to the constrains of the tools described herein. The present invention thus has the advantage of considerable flexibility for the usage of any number of future tests and testing protocols.

Further Analysis & Biobanking

When the system 100 is used and a cancer cell is detected, the information is stored on, for example, a mobile app, which is setup to alert the physician, e.g., within a memory in the portable device, generally designated by the reference numeral 126, and processed using a processer, generally designated by the reference numeral 128. The patient may elect for further analysis of the sample, which they can discuss and order through their prescribing physician. The device kit 105 preferably contains a storage vehicle 130 to preserve the sample in a stable and intact format for later analysis and likely shipping or other transport.

After use, the cartridge 110 is simply removed from the phone jack 122 and placed in the provided container 130, which preferably contains at least one stabilizing agent. Instructions may vary depending on the intended use of the kit 105, for example, a kit 105 used to monitor metastatic breast cancer in hospitalized patients has a different storage protocol than a kit 105 being used by Doctors working in remote parts of the world with difficult conditions, or a home test kit.

The samples can then be further analyzed at an accredited laboratory using a number of sequencing technologies, such as qPCR or NGS in order to obtain knowledge on the genetic alterations and mutations in the patient's cancer. Knowledge of the genetic alterations of a cancer can help determine an appropriate treatment plan. In particular, targeted therapies are therapies that are effective only for people whose cancer cells have specific genetic alterations that cause the cells to grow out of control, which are called driver mutations. As an example, mutations in the EGFR gene that make cells divide rapidly are found in some people's lung cancer cells. A patient whose lung cancer cells contain an EGFR may respond well to inhibitor drugs as opposed to a modality of chemotherapy. Clinical tumor DNA sequencing can reveal whether a patient's lung tumor has an EGFR mutation.

As discussed, the invention kit 105 preferably contains a storage vehicle 130 designed to maintain the integrity of the sample(s) collected on the chip cartridge(s) 110 until transported or shipped to a laboratory facility, where the cell DNA/RNA can then be extracted, and the sample library is prepared for use in a sequencing machine for analysis. The Physician receives the results to then discuss treatment options with the patient.

Programs such as The Cancer Genome Project and the Cancer Genome Atlas can benefit from the large volume of de-identified data which will obtained from samples collected on the proposed Invention.

Device Manufacture

Development of the invention may entail series of miniaturization steps, exemplified embodiments of which are outlined below. It should, of course, be understood that alternative configurations to the below illustrations are possible.

First, initially: an array of 76 antibody-nanotube microelectrodes on laboratory bench, back-wired to an analog-to-digital board, generally designated by the reference numeral 119. Electrical signals measured digitally by USB connection to a desktop or laptop computer, generally designated by the reference numeral 140, instead of the aforesaid mobile phones, with installed signal analysis algorithm. As shown, both wireless 142 and wireline 144 connectivity is possible also in the practice of the present invention. Cells can be manually eluted from each microelectrode for microscopy, RNA, or DNA analysis. One can also capture ct-DNA using this device.

Second, next generation: an array of 360 antibody-nanotube microelectrodes are back-wired to an analog-to-digital board 119, contained in a grounded polymer box. Electrical signals are measured digitally by USB connection to the laptop 140 or tablet or home computer or other computing device with installed signal analysis algorithm. Cells can be manually eluted from each microelectrode for microscopy, e.g., for RNA or DNA analysis.

The Third generation: a miniaturized array of 360 antibody-nanotube microelectrodes are back-wired to an integral analog-to-digital component 119 and mounted on a sterilizable polymer block for micro USB connection to a smartphone 120 with installed signal analysis algorithms. The Array can then be sent to central facility for robotic or other elution of cells from each microelectrode for automated microscopy, e.g., for RNA or DNA analysis.

Exemplary Applications

Monitoring Response to Therapy

Typically it takes up to six months after beginning a course of therapy to evaluate the efficacy of the treatment. For adjuvant chemotherapy it takes 4-6 months. Utilizing the proposed invention would enable the physician to monitor the patient's tumor counts at regular intervals to track increasing or depleting CTC counts. Physicians can determine earlier whether therapy is working or if the treatment should be altered.

Monitoring Remission

Patients in remission can benefit from regular non-invasive testing conducted in a comfortable setting in collaboration with their oncologist to obtain confirmation that they are in fact clear of cancer, as opposed to radiological or surgical testing in a hospital setting.

Screening as Part of an Annual or Other Health Check

In an annual checkup, the Doctor looks at your vital signs, asks you lifestyle questions, listens to your pulse, checks your blood pressure and discusses any issues you may be having. Given the low cost, ease of use and non-invasive nature of the present invention, testing for cancer can now be a routine part of your check up, particularly when patients present with risk factors, such as smoking, obesity, family history, or a genetic predisposition to cancer Screening can also be done in remote areas through programs such as Doctors Without Borders Consumer initiated screening may also be accomplished with a physician's order.

Screening for High-Risk Populations

High-risk populations most often do not have access to healthcare, such as the homeless, drug addicts, those living by prostitutes and people living in war zones. There are organizations that attempt to provide aid to these groups, but are limited in the care they can offer such as non-profits, charitable organizations, and government initiatives. Sometimes, these high risk and low income population do not seek medical care due to costs associated. The present technology overcomes this deficit and would be highly useful for Medicare, Medicaid and other non-profit organizations worldwide.

It should be understood that although blood fluids are mentioned in the exemplary embodiments, the present invention contemplates the usage of other bodily fluids as well, particularly if those bodily fluids would include indications or markers for cancer, e.g., urine, menstrual flow, semen, spit, sweat and other bodily fluids may thus be employed where applicable and with the appropriate test kit 105 designed for that fluid. Of course, test kits 105 may include multiple capabilities and multiple instructions, which could also be downloaded off the Internet.

The previous descriptions are of preferred embodiments for implementing the invention, and the scope of the invention should not necessarily be limited by these descriptions. It should be understood that all articles, references and citations recited herein are expressly incorporated by reference in their entirety. The scope of the current invention is defined by the following claims.

What is claimed is:

1. A cartridge for cancer detection comprising:
an adaptor configured to connect said cartridge to a hand-held device;
a fluid receptor configured to receive an amount of fluid therein;
a plurality of cancer detection biomarkers, said plurality of cancer detection biomarkers disposed in communication with said fluid receptor and targeted for a specific cancer,
wherein, upon contact of said amount of fluid to at least one of said cancer detection biomarkers, a reaction occurs, said reaction producing a plurality of analog signals;
a plurality of nanotubes, said plurality of nanotubes configured to receive said plurality of analog signals produced during said reaction, at least one of said nanotubes conducting respective analog signals therethrough; and
a converter, said converter connected to said plurality of nanotubes and converting said respective analog signals to a plurality of digital signals,
wherein said plurality of digital signals correspond to said specific cancer.

2. The cartridge for cancer detection according to claim 1, wherein said adaptor is configured to connect to at least one port of said device.

3. The cartridge for cancer detection according to claim 2, wherein said at least one port is a USB port.

4. The cartridge for cancer detection according to claim 1, wherein said device is selected from the group consisting of an Android phone, an iPhone, a laptop computer, a tablet, and combinations thereof.

5. The cartridge for cancer detection according to claim 1, wherein said cartridge includes at least one wafer chip.

6. The cartridge for cancer detection according to claim 1, wherein said converter comprises an analog-to-digital board.

7. The cartridge for cancer detection according to claim 1, wherein said plurality of cancer detection biomarkers test for circulating tumor cells (CTCs).

8. The cartridge for cancer detection according to claim 1, wherein said plurality of cancer detection biomarkers are selected from the group consisting of human epidermal growth factor receptor-2 (HER2/neu, c-erbB2) (HER-2), epithelial cell adhesion molecule (EpCAM), epidermal growth factor receptor (EGFR), Vimentin, and combinations thereof.

9. The cartridge for cancer detection according to claim 1, wherein said amount of fluid is a drop.

10. The cartridge for cancer detection according to claim 1, wherein said fluid is selected from the group consisting of blood, urine, menstrual flow, semen, spit, sweat and combinations thereof.

11. A kit for cancer detection comprising:
at least one instruction for the use of said kit; and
a cartridge, said cartridge comprising:
an adaptor configured to connect said cartridge to a hand-held device;
a fluid receptor configured to receive an amount of fluid therein;

a plurality of cancer detection biomarkers, said plurality of cancer detection biomarkers disposed in communication with said fluid receptor and targeted for a specific cancer, wherein, upon contact of said amount of fluid to at least one of said cancer detection biomarkers, a reaction occurs, said reaction producing a plurality of analog signals;

a plurality of nanotubes, said plurality of nanotubes configured to receive said plurality of analog signals produced during said reaction, at least one of said nanotubes conducting respective analog signals therethrough; and a converter, said converter connected to said plurality of nanotubes and converting said respective analog signals to a plurality of digital signals, wherein said plurality of digital signals correspond to said specific cancer.

12. The kit for cancer detection according to claim 11, wherein said at least one instruction is obtained from an application or app.

13. The kit for cancer detection according to claim 11, wherein said adaptor is configured to connect to at least one port of said device.

14. The kit for cancer detection according to claim 13, wherein said at least one port is a USB port.

15. The kit for cancer detection according to claim 11, wherein said device is selected from the group consisting of an Android phone, an iPhone, a laptop computer, a tablet, and combinations thereof.

16. The kit for cancer detection according to claim 11, wherein said cartridge includes at least one wafer chip.

17. The kit for cancer detection according to claim 11, wherein said converter comprises an analog-to-digital board.

18. The kit for cancer detection according to claim 11, wherein said plurality of cancer detection biomarkers test for circulating tumor cells (CTCs).

19. The kit for cancer detection according to claim 11, wherein said plurality of cancer detection biomarkers are selected from the group consisting of human epidermal growth factor receptor-2 (HER2/neu, c-erbB2) (HER-2), epithelial cell adhesion molecule (EpCAM), epidermal growth factor receptor (EGFR), Vimentin, and combinations thereof.

20. The kit for cancer detection according to claim 11, wherein amount of fluid is a drop.

21. The kit for cancer detection according to claim 11, wherein said fluid is selected from the group consisting of blood, urine, menstrual flow, semen, spit, sweat and combinations thereof.

22. The kit for cancer detection according to claim 11, further comprising:

at least one storage container, said at least one storage container configured to house a plurality of said cartridges therein.

23. The kit for cancer detection according to claim 11, further comprising:

a finger pricking device and antiseptic wipes.

24. A method for detecting cancer comprising:

depositing a fluid sample from a patient on a detection area of a cartridge;

analyzing, within said cartridge, said fluid sample against at least one antigen for a specific cancer;

detecting, by at least one of a plurality of nanotubes disposed in communication with said detection area, analog signals indicative of said specific cancer in said fluid sample;

converting, by a converter, said analog signals to a plurality of digital signals; and forwarding said plurality of digital signals to a hand-held device.

25. The method for cancer detection according to claim 24, further comprising:

unconnecting said cartridge from said hand-held device; and depositing said cartridge in a storage container.

* * * * *